(12) United States Patent
Shahinpoor et al.

(10) Patent No.: US 6,405,532 B1
(45) Date of Patent: Jun. 18, 2002

(54) METAL HYDRIDE ARTIFICIAL MUSCLES

(75) Inventors: Mohsen Shahinpoor; Kwang J. Kim, both of Albuquerque, NM (US)

(73) Assignee: Environmental Robots, Inc., Albuquerque, NM (US)

( * ) Notice: Subject to any disclaimer, the term of this patent is extended or adjusted under 35 U.S.C. 154(b) by 0 days.

(21) Appl. No.: 09/909,548

(22) Filed: Jul. 19, 2001

Related U.S. Application Data
(60) Provisional application No. 60/220,006, filed on Jul. 21, 2000.

(51) Int. Cl.$^7$ ................................................ F01B 29/10
(52) U.S. Cl. .......................................... 60/512; 60/515
(58) Field of Search .......................... 60/508, 512, 513, 60/515

(56) References Cited

U.S. PATENT DOCUMENTS

| | | | | |
|---|---|---|---|---|
| 4,439,111 A | * | 3/1984 | Seidel et al. ................. | 417/379 |
| 4,826,741 A | * | 5/1989 | Aldhart et al. ................ | 429/19 |
| 5,250,167 A | | 10/1993 | Adolf et al. | |
| 5,334,629 A | * | 8/1994 | Zirino ........................ | 523/137 |
| 5,389,222 A | | 2/1995 | Shahinpoor | |
| 5,531,473 A | * | 7/1996 | Rink et al. ................... | 280/737 |
| 5,821,664 A | | 10/1998 | Shahinpoor | |

OTHER PUBLICATIONS

M. Shahinpoor, Y. Bar–Cohen, J. Simpson, and J. Smith, "Ionic Polymer–Metal Composites (IPMC's) As Biomimetic Sensors, Actuators and Artificial Muscles—A Review", Smart Materials & Structures Journal, vol. 7, pp. R15–R30 (1998).

G. Wang and M. Shahinpoor, "Design, Prototyping and Computer Simulation of a Novel Large Bending Actuator Made with A Shape Memory Alloy Contractile Wire", Smart Materials and Structures Journal, vol. 6, No. 2, pp. 214–221 (1997).

G. Wang and M. Shahinpoor,"Design for Shape Memory Alloy Rotatary Joint Actuators Using Shape Memory Effect and Pseudoelastic Effect" Smart Materials Technology, Edited by W. Simmons, Iihan Aksay and D.R. Huston, SPIE Publication vol. 3040, pp. 23–30 (1997).

G. Wang and M. Shahinpoor, "A New Design for a Rotatary Joint Actuator Made with Shape Memory Allowy Contractile Wire", J. Intelligent Materials Systems & Structures, vol. 8, No. 3, pp. 215–219, Mar. 1997.

M. Shahinpoor, "Electrically–activated artificial muscles made with liquid crystal elastomers", Paper No. 3987–27, SPIE Smart Materials & Structures Conference, New Port Beach, CA, Mar. 5–9 (2000).

M. Shahinpoor, "Ionic Polymer Metal Composite as Biomimetic Sensors and Actuators" in Polymer Sensors and Actuators, edited by Y. Osada and D. DeRossi, Springer–Verlag Publishing, Springer, Berlin–Heidelberg, pp. 325–360 (1999).

Houston, E.L. and G.D. Sandrock "Engineering Properties of Metal Hydrides", Journal of the Less–Common Metals, vol. 74, pp. 435–443, 1980.

Kim. K.J., K.T. Feldman, Jr., G. Lloyd, and A. Razani, "Compressor–Driven Heat Pumps Development Employing Porous Metal Hydride Compacts", ASHRAE Transactions, 1998–Winter Meeting, San Francisco, vol. 104, Pt. 1, SF–98–18–4, 1998a.

(List continued on next page.)

*Primary Examiner*—Hoang Nguyen
(74) *Attorney, Agent, or Firm*—Dennis F. Armijo

(57) ABSTRACT

New artificial muscles and actuators, that are operated by hydrogen gas as working fluid stored interstitially in metal hydrides as a hydrogen sponge. These artificial muscles and actuators are operated both electrically and thermally. The artificial muscles and actuators have fast response, are compact/light-weight, are noiseless, and produce high-power density. They can be used for biomedical, space, defense, micro-machines, and industrial applications.

26 Claims, 9 Drawing Sheets

OTHER PUBLICATIONS

Kim, K.J., G. Lloyd, A. Razani, and K.T. Feldman, Jr., "Development of LaNi$_5$/Cu/Sn Metal Hydride Powder Composites", Powder Technology–An International Journal, in press, 1998b.

Kim, K.J., K.T. Feldman, Jr., G. Lloyd, and A. Razani, "Performance of High Power Metal Hydride Reactors", International Journal for Hydrogen Energy, vol. 23, No. 5, pp. 355–362, 1998c.

Kim, K.J., T. Feldman, Jr., G. Lloyd, and A. Razani, "Thermal Analysis of the Ca$_{0.4}$Mm$_{0.6}$Ni$_5$ Metal–Hydride Reactors," Applied Thermal Engineering, vol. 18, No. 12, pp. 1325–1336, 1998d.

Muller, W.M., J.P. Blackledge, and G.G. Libowitz, Metal Hydrides, Academic Press, 1968.

* cited by examiner

METAL HYDRIDE ARTIFICIAL MUSCLES

CROSS-REFERENCE TO RELATED APPLICATIONS

This application is based on U.S. Provisional Application Ser. No. 60/220,006 entitled "Novel Metal Hydride Artificial Muscles", filed on Jul. 21, 2000, the teachings of which are incorporated herein by reference.

BACKGROUND OF THE INVENTION

1. Field of the Invention (Technical Field)

The invention relates to artificial muscles and more particularly to artificial muscles actuated by a hydrogen gas as a working fluid and metal hydrides as a hydrogen sponge and can be operated both electrically and thermally.

2. Background Art

Materials and devices that can mimic biological muscles and thus be considered as artificial muscles have been discussed in the pertinent literature. There are prior art artificial muscles using ionic polymers as disclosed in M. Shahinpoor, Y. Bar-Cohen, J. Simpson, and J. Smith, "Ionic Polymer-Metal Composites (IPMC's) As Biomimetic Sensors, Actuators and Artificial Muscles-A Review", Smart Materials & Structures Journal, Vol. 7, pp. R15–R30, (1998); M. Shahinpoor, "Ionic Polymer Metal Composite As Biomimetic Sensors and Actuators", in Polymer Sensors and Actuators, edited by Y. Osada and D. DeRossi, Springer-Verlag Publishing, Springer, Berlin-Heidelberg, pp. 325–360, (1999).

In addition, shape memory alloy artificial muscles have been disclosed in M. Shahinpoor, "Fibrous, Parallel Spring-Loaded Shape-Memory Alloy (SMA) Robotic Linear Actuators", U.S. Pat. No. 5,821,664, issued Oct. 13th, 1998; G. Wang and M. Shahinpoor, "Design, Prototyping and Computer Simulation of A Novel Large Bending Actuator Made with A Shape Memory Alloy Contractile Wire", Smart Materials and Structures Journal, Vol. 6, No. 2, pp. 214–221, (1997); G. Wang and M. Shahinpoor, "Design for Shape Memory Alloy Rotatory Joint Actuators Using Shape Memory Effect and Pseudoelastic Effect", Smart Materials Technology, Edited by W. Simmons, Ilhan Aksay and D. R. Huston, SPIE Publication Vol.3040, pp. 23–30, (1997); and G. Wang and M. Shahinpoor, "A New Design for A Rotatory Joint Actuator Made with Shape Memory Alloy Contractile Wire", J. Intelligent Materials Systems & Structures, Vol. 8, no. 3, pp. 215–219, March (1997).

Liquid crystal elastomer artificial muscles are discussed in M. Shahinpoor, "Electrically-activated artificial muscles made with liquid crystal elastomers", paper no. 3987-27, SPIE Smart Materials & Structures Conference, New Port Beach, Calif., Mar. 5–9, (2000).

Other types of artificial muscles are discussed in U.S. Pat. No. 5,250,167 entitled Electrically Controlled Polymeric Gel Actuators; and U.S. Pat. No. 5,389,222 entitled Spring-Loaded Ionic Polymeric Gel Linear Actuator.

However, none of the prior art discloses metal hydride artificial muscles.

SUMMARY OF THE INVENTION (DISCLOSURE OF THE INVENTION)

In accordance with the present invention there is provided a method and apparatus for using metal hydrides for an artificial muscle system. The preferred metal hydride artificial muscle comprises an expandable bladder, at least one metal hydride specimen encased within the expandable bladder and an apparatus to heat the at least one metal hydride. The preferred expandable bladder also comprises a collapsible bladder. The preferred expandable bladder comprises a hermetically sealed bladder. The expandable bladder can further comprise at least one actuator arm affixed to at least one part of said expandable bladder and can also comprise spring loading the at least one actuator arm. The preferred at least one metal hydride specimen comprises encapsulated particles within the at least one metal hydride specimen. The preferred encapsulated particles comprise an encapsulated material comprising a thermally conductive medium. The preferred apparatus to heat the at least one metal hydride comprises a controller. The preferred controller comprises a temperature sensor feedback loop. The controller can also comprise a microprocessor. The apparatus to heat the at least one metal hydride specimen can comprise an electric Joule heater. The preferred apparatus to heat the at least one metal hydride specimen comprises a heater to heat the at least one metal hydride specimen above at least one critical temperature. The apparatus to heat the at least one metal hydride specimen can further comprise an apparatus to cool the at least one metal hydride specimen. The preferred apparatus to cool the at least one metal hydride specimen comprises an apparatus to cool the at least one metal hydride specimen to below at least one critical temperature.

The preferred method for actuating an object with a metal hydride artificial muscle comprising the steps of providing at least one metal hydride specimen in an expandable bladder, affixing at least one part of the expandable bladder to an actuator arm and heating the at least one metal hydride specimen. The step of heating comprises heating the at least one metal hydride specimen above at least one critical temperature. The preferred method further comprises the step of cooling the at least one metal hydride specimen. The preferred step of cooling comprises cooling the at least one metal hydride specimen below at least one critical temperature. The step of heating preferably comprises controlling a heater. The step of controlling comprises sensing a temperature of the at least one metal hydride and feeding the sensed temperature to the controller. The method can also comprise the step of spring loading the at least one actuating arm. The preferred step of providing at least one metal hydride specimen comprises encapsulating particles within the at least one metal hydride specimen with a thermally conductive medium.

The preferred metal hydride artificial muscle for biomedical and robotic applications comprises an expandable bladder with a first end affixed to a first portion of a body and a second end affixed to a second portion of a body, at least one metal hydride specimen encased by the expandable bladder and an apparatus for heating and cooling the at least one metal hydride specimen.

The preferred metal hydride artificial muscle for hydrogen gas aided take off, flying and landing of an object, comprises a bladder, at least one metal hydride specimen encased by the bladder, and an apparatus for heating and cooling the at least one metal hydride specimen.

The preferred metal hydride artificial muscle joint power augmentation system for external assistance of a person comprises an expandable and collapsible bladder with a first end affixed to a first portion of the area to be augmented and a second end affixed to a second portion of the area to be augmented, at least one metal hydride specimen encased by the expandable and collapsible bladder and an apparatus for heating and cooling the at least one metal hydride specimen.

The joint power augmentation system can comprise a joint power augmentation system for astronaut space suits.

A primary object of the present invention is to provide a new family of artificial muscles capable of actuating with a broad range of applications.

Yet another object of the present invention is to provide electrical and thermal robotic control capabilities.

Yet another object of the present invention is to mimic biological situations that require high force, power, and velocity responses.

A primary advantage of the present invention is that it provides biological-like smooth operation capability with long stroke capabilities of actuation along with large forces.

Another advantage of the present invention is that it is noiseless and vibrationless.

Yet another advantage of the present invention is that the functioning mechanism is the simultaneous hydrogen absorption/desorption and can lead to a buffering effect preventing sharp power surge or shock loads.

Another advantage of the present invention is that in selecting an appropriate hydride, the desired operating pressure can be easily obtained.

Another advantage of the present invention is that it can also provide a large actuation-displacement.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

A new artificial muscle is disclosed that is biorobotic, noiseless, compact/light-weight, fast actuation, high-powered, biocompatible, and environmentally clean. The new metal hydride artificial muscles (MHAM's) are actuated by hydrogen gas as a working fluid and metal hydrides as hydrogen sponge and can be operated both electrically and thermally. These MHAM's have immediate applications for biomedical, space, micro-machines and other industries. Therefore, they can be. used as micro-to-macro scale applications.

The large uptake/discharge capacity of hydrogen in metal hydrides, for example, the volume of hydrogen gas equal to approximately 1,000 times metal hydride, and their rapid kinetics provide MHAM's applications as being noiseless, having fast response, being compact/light-weight, and having high-power. Metal hydrides can absorb or store and desorb or release a large amount of hydrogen gas to obtain significantly high mechanical energy. A MHAM's application unit can be highly compact and ultra light as opposed to current state-of-the-art actuators. Fast actuation time can be obtained, such as 1 Hz for heating/cooling switching.

Figures 1A, 1B:
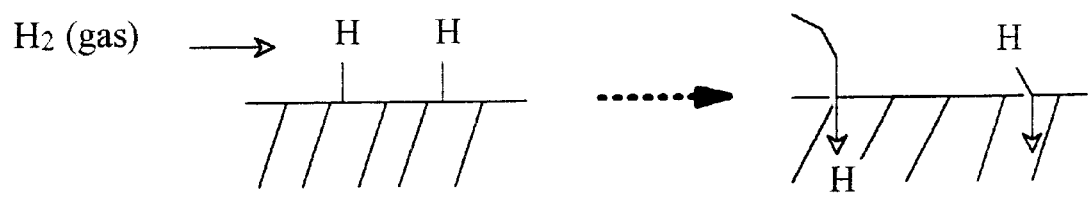
FIG. 1A illustrates the chemisorption by a metal hydride onto the surface.
FIG. 1B illustrates the hydriding reaction of a metal hydride.

Metal hydrides are the binary combination of hydrogen and a metal or metal alloy. They can absorb large amounts of hydrogen via surface chemisorption and subsequent hydriding reactions as illustrated in FIGS. 1A and 1B. At a given temperature metal hydrides form condensed phases with hydrogen upon the partial pressure of hydrogen present. The useful characteristics of metal hydrides are the large uptake/discharge capacity of hydrogen, safe operation because hydrogen desorption is an endothermic process, rapid kinetics, and they are environmentally clean. They have been used for a long time for hydrogen storage and for thermal devices.

Figure 2A:
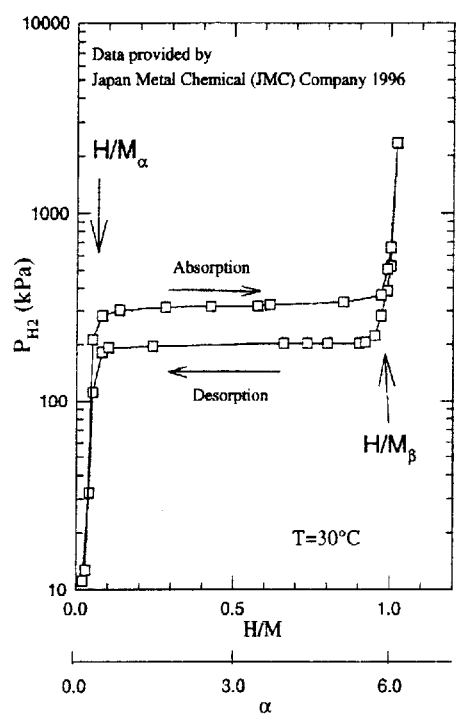
FIG. 2A is a van't Hoff plot of $LaNi_5$ showing pressure vs. atom ratio.
Figure 2B:
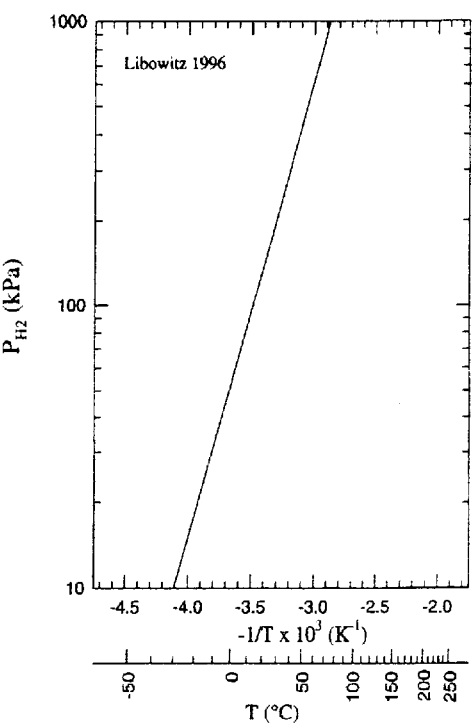
FIG. 2B is a van't Hoff plot of $LaNi_5$ showing pressure vs. negative inverse temperature.

The equilibrium composition of metal hydrides is of interest. In most metal hydrides, there are two distinct phases, $\alpha$ and $\beta$ phases, as shown in FIGS. 2A and 2B. An isotherm gives the absolute equilibrium absorption or desorption pressure as a function of the hydrogen concentration, H/M (M=metal atom). Initially, hydrogen dissolves within the solid lattice of the metal hydride. Continued addition of hydrogen results in a sample consisting of the chemisorbed phase. All interstitial hydrogen is chemically combined in the solid lattice. The endpoints, $H/M_\alpha$ and $H/M_\beta$ are called the phase limits of the plateau region. They are generally not sharply defined. In a dehydriding or desorption process frequently hysteresis is observed, with the dehydriding isotherm lying slightly below the hydriding isotherm.

A typical metal hydride is the rare-earth intermetallic $LaNi_5$ (lanthanium-pentanickel). The hydriding/dehydriding reaction can be written as, $$LaNi_5 + \frac{x}{2}H_2 \Leftrightarrow LaHi_5H_x + \Delta H_a \qquad (1)$$

where x and $\Delta H_a$ are non-stoichiometric constant which is about 6–6.7 for this particular compound and the heat of absorption giving off ($-3.1 \times 10^4$ kJ/kgmole of $H_2$, for $LaNi_5$), respectively. It is usually close to the heat of desorption, $\Delta H_d$). The equilibrium behavior of metal hydrides in the plateau region can be described by van't Hoff plots as shown in FIGS. 2A and 2B, according to the following relation, $$ln P_{H2}(atm) = \frac{\Delta H_a}{RT} - \frac{\Delta S}{R} \quad (2)$$

where R is the molar gas constant, equal to 8.314 kJ/kgmole-K, T is the absolute temperature in K, $\Delta H_a$ is the heat of absorption in kJ/kgmole of $H_2$, and $\Delta S$ is the standard entropy of formation in kJ/kgmole of $H_2$-K. The van't Hoff plots and the static p-H/M-T data available for particular metal hydrides are the usual basis for thermo-mechanical design. FIGS. 2A and 2B also shows the van't Hoff plots for $LaNi_5$. Depending upon pressure/temperature requirements and available temperature desired hydrides could be selected for a use in various artificial muscle systems.

Figures 3A, 3B:
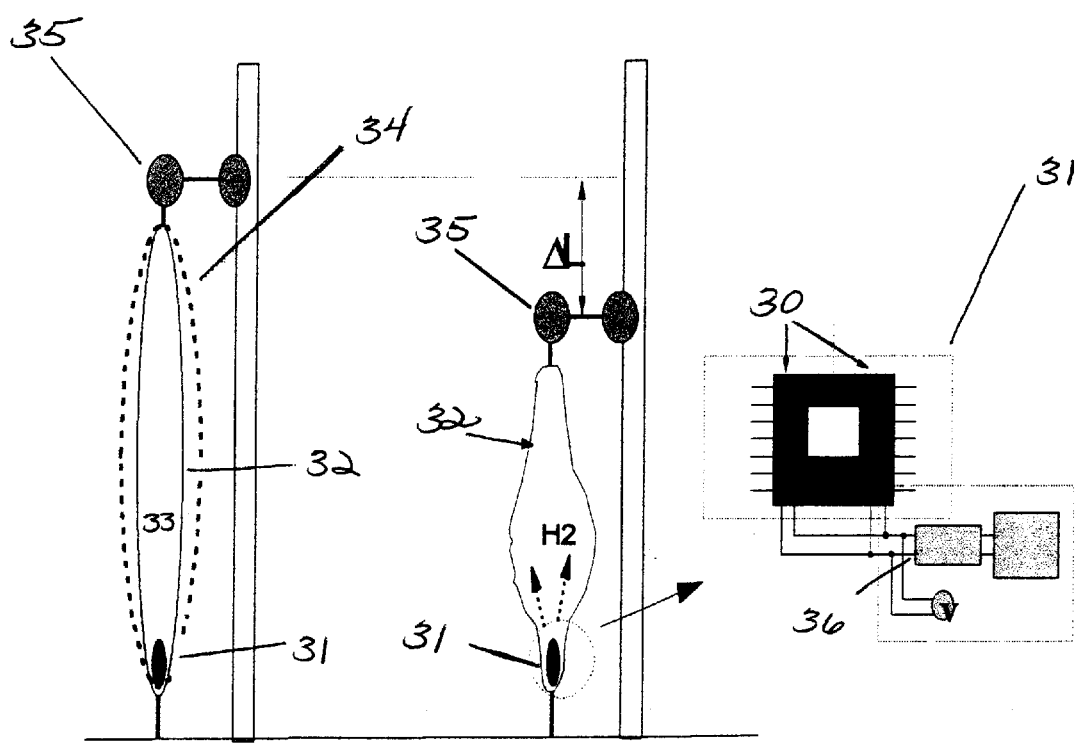
FIG. 3A shows a configuration of the preferred embodiment of the invention.
FIG. 3B is an expanded view of the metal hydride of FIG. 3A.

The principle of the metal hydride artificial muscles (MHAM's) is shown in FIGS. 3A and 3B. The MHAM functions using hydrogen gas pressure from the metal hydride by manipulating thermoelectric input. The thermoelectric elements 30 are located near the metal hydride unit 31 to provide appropriate heat sources, either heating or cooling, by simply changing the direction of electric current to the element 30. The expandable inner bladder polymeric material 32, such as Manosil™ silicon rubber, that contains the hydrogen gas 33 constructs the functioning part. The key parameter of the expandable material 32 is the capability to sustain repeated strains of over 300%. A rubber material is used since it can manage large strains with nearly no plastic strain and creep. When heat is applied to the metal hydride unit 31, hydrogen gas 33 is immediately desorbed from the metal hydride unit 31. Then, the functioning part or the shell 34 contracts while the polymeric material 32 expands under constant pressure, causing pulling force between the endpoints 35 as designated as $\Delta L$. The maximum force at a given pressure is obtained when the shell 34 is pulled out as far as possible. The relationship between pressure and force is nearly linear at constant extensions. In fact, this allows the movement distance $\Delta L$ to be set by regulating the $H_2$ pressure in the system by controlling heat input to the metal hydride unit 31. When metal hydride unit 31 is cooled, the hydrogen gas 33 moves back to the metal hydride unit 31 being absorbed. Therefore, internal pressure decreases and the shell 34 goes back to the starting position. A computer controller 36, such as a microprocessor or the like, of the metal hydride system can accelerate its performance. The computer controller 36 preferably has a current control with temperature sensing with feedback. Therefore, the amount of $H_2$ discharged and the internal pressure can be automatically controlled. In Table 1, the properties of the metal hydride artificial muscles are briefly compared with shape memory alloys and electrostrictive or magnetostrictive ceramic actuators.

TABLE 1

Properties of Interest for a Number of Different Types of Actuators

| Property | Metal Hydride Artificial Muscles | Shape Memory Alloys (SMA) | Typical Electrostrictive or Magnetostrictive Ceramics |
|---|---|---|---|
| Actuation Displacement | >1000% | <8% short fatigue life | 0.1–0.3% |

TABLE 1-continued

Properties of Interest for a Number of Different Types of Actuators

| Property | Metal Hydride Artificial Muscles | Shape Memory Alloys (SMA) | Typical Electrostrictive or Magnetostrictive Ceramics |
|---|---|---|---|
| Stress (MPa) | 0.1–100 | About 700 | 30–40 |
| Reaction speed | msec to sec | sec to min | $\mu$ sec to msec |
| Density | 3–8 g/cc | 5–6 g/cc | 6–8 g/cc |
| Drive voltage | N/A | N/A | 50–800 V |

The manufacturing process for the preferred metal hydrides is essential. In most metal hydrides undergoing absorption/desorption cycles, high volumetric strain lead to decrepitation of metal hydrides into a powdered bed of micron-sized particles. Although metal hydrides themselves have rapid intrinsic kinetics, the poor thermal conductivity of such powder beds ($k_{eff}$~0.1 W/m-k) limits the heat transfer communication with the beds, therefore, retards the apparent kinetics. To obtain reasonably rapid kinetics, actuator fabrication must improve the thermal conductance of the unit.

Typically, metal hydride particles are sieved to a diameter of 25–45 micrometer and then micro-encapsulated with a thin copper using an electroless plating technique. In general, electroless plating technique refers to chemical processes in which a metal as an ion in aqueous solution is reduced to the metallic state by means of a chemical reducing agent. The favorable electron transfer reaction would be,

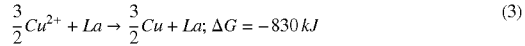

$$\frac{3}{2}Cu^{2+} + La \rightarrow \frac{3}{2}Cu + La; \Delta G = -830 kJ \quad (3)$$

Then, the standard reaction indicates a transfer of 3 moles of electrons per unit mole of $LaNi_5$. The process that has been developed uses a simple/inexpensive solution prepared with $H_2SO_4$ and $CuSO_4$ and shows a homogeneous ion exchange occurred that reduces the $Cu^{+2}$ anion. Since the Gibb's free energy is negative, the process is thermodynamically feasible.

Figure 4A:
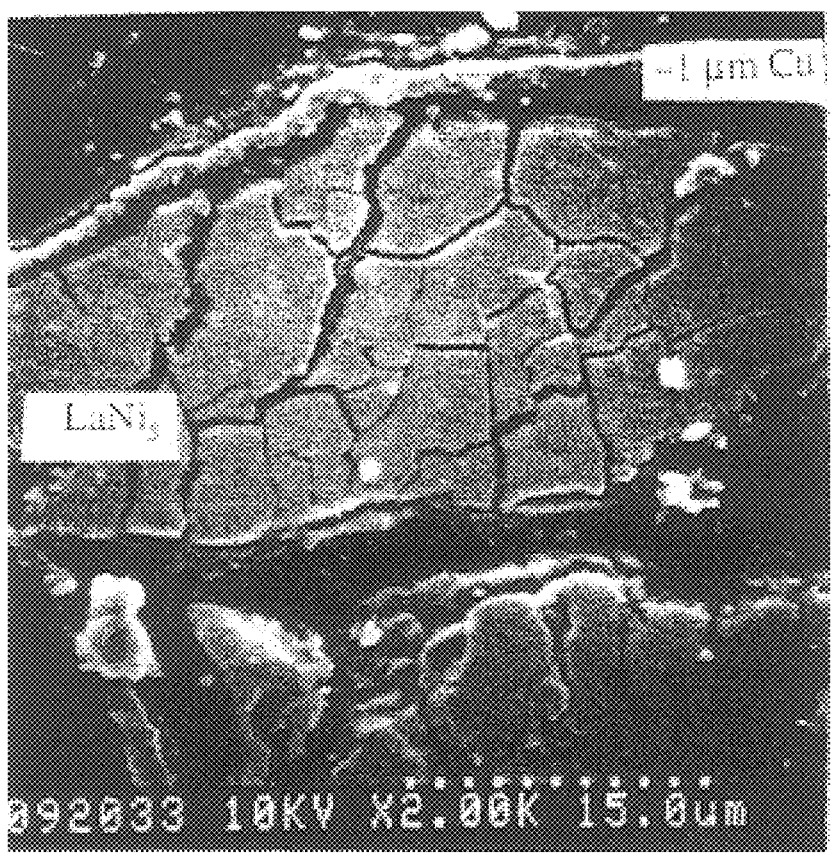
FIG. 4A shows a $LaNi_5$ particle ($D_p$~40 micron) encapsulated by a thin copper shell.
Figure 4:
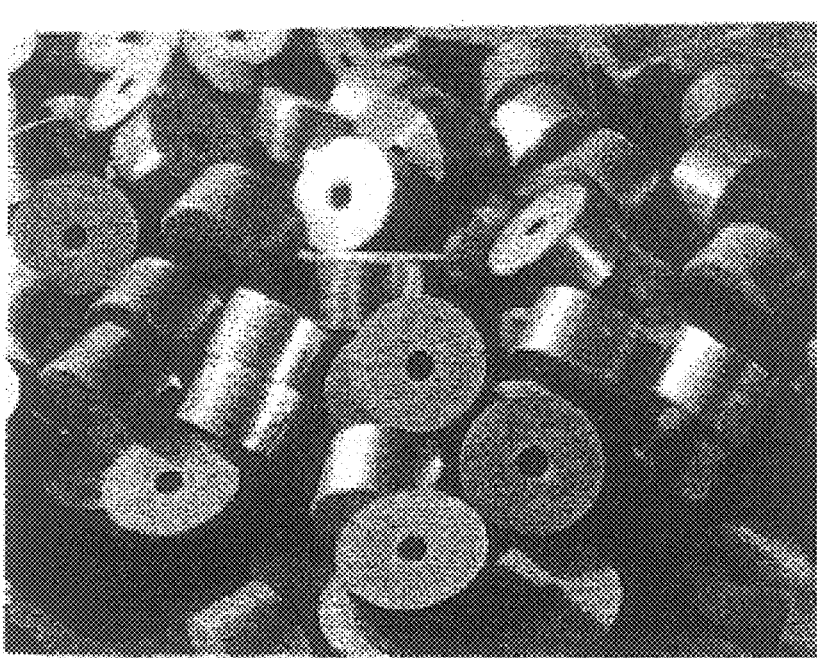
FIG. 4B is depicts the manufactured porous metal hydride compact.

In FIG. 4A, a $LaNi_5$ particle ($D_p$~40 micron) encapsulated by a thin copper shell is shown. $LaNi_5$ particles were initially manufacturer-sieved, cleaned, and then copper plated by using an electroless method described above in a batch reactor. The condition for compaction is 5 kpsi. A photograph of manufactured porous metal hydride compact is also provided in FIG. 4B.

Figure 5:
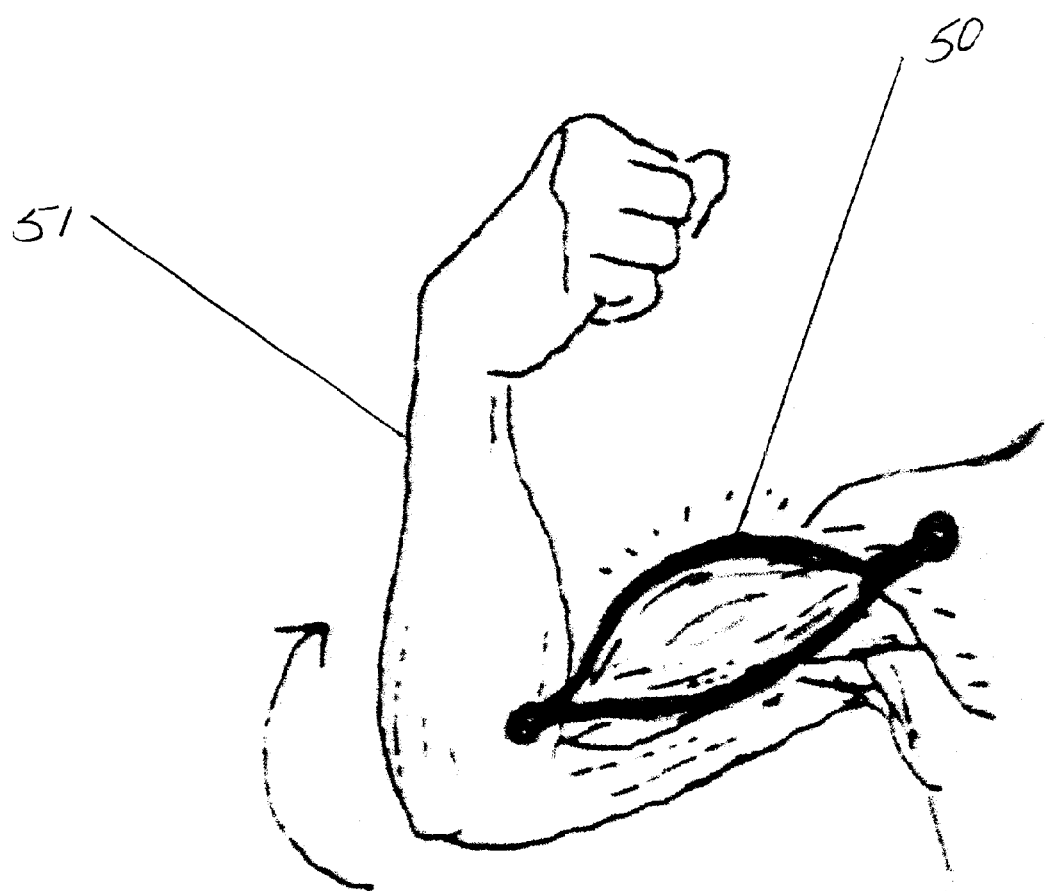
FIG. 5 shows a biorobotic arm.

The new metal hydride artificial muscle invention can be used as a biorobotic arm as shown in FIG. 5. In this configuration, initially, the metal hydride artificial muscle 50 is resting. The biorobotic arm 51 is bent when the metal hydride biorobotic actuator is in action for contraction. The sequence is reversed for stretching.

Figure 6:
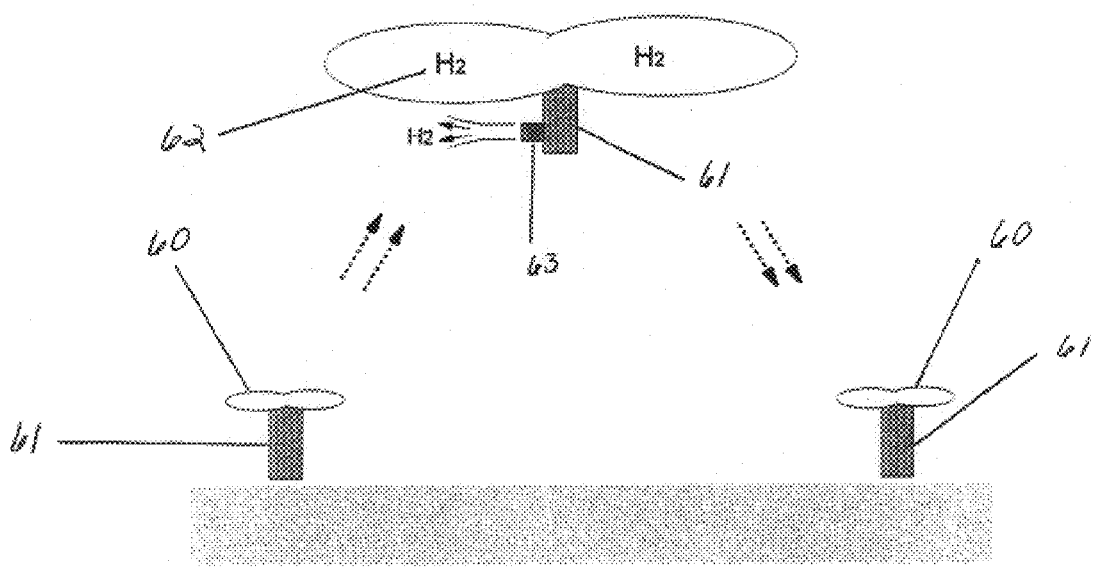
FIG. 6 is a schematic of the flying high-power metal hydride system.

The present invention can also be used as a taking-off and landing metal hydride actuator. A schematic of the flying high-power metal hydride system is given in FIG. 6. A typical miniaturized balloon 60 has a set fully inflated diameter, for example 2 ft. It consists of an inflatable balloon 60 equipped with a metal hydride actuation unit 61 that releases hydrogen gas 62 upon being activated by any means of heating, such as solar irradiation, laser or Joule heating. Once the balloon 60 starts to inflate, the balloon 60 takes off. One feature of such a flying system is that, as the balloon 60 raises its flying height level, it senses the ambient temperature that typically gets cooled. As a consequence, a portion of hydrogen gas 62 moves back to the metal hydride unit 61. Then, the buoyancy force is reduced to lower its flying altitude. Implementing this feature creates a potential for a flying machine for uses in both defense and commercial applications. Hydrogen gas 62 out of metal hydride actuator 61 can also be used for the propulsion unit 63.

Figure 7:
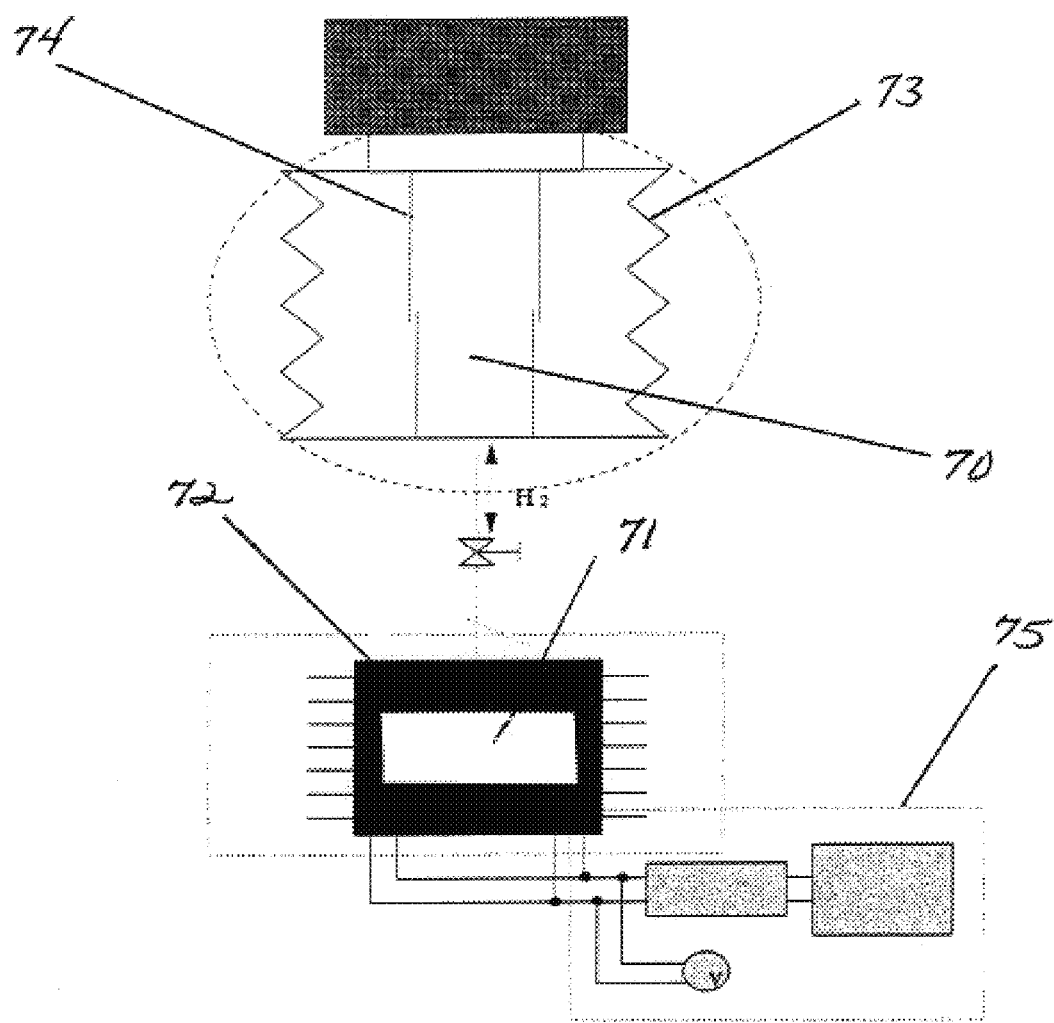
FIG. 7 depicts the actuator configuration of the metal hydride artificial muscle.

The present invention can also be used as a cylindrical actuator. The cylindrical actuator configuration of the metal hydride artificial muscle is schematically shown in FIG. 7. This embodiment functions using hydrogen gas 70 pressure from the metal hydride 71 by manipulating thermoelectric input 72. The thermoelectric input can be any kind of heating/cooling elements such as heat radiation panels and direct/indirect heat exchangers. The heat input device or thermoelectric elements 72 with controller 75 are located near the metal hydride 71 to provide appropriate heat or cooling sources by simply changing the direction of electric current to the element 72. Metal bellows 73 or a soft inflation material that contains the hydrogen gas 70 comprises the functioning part. When heat is applied to the metal hydride 71, hydrogen gas 70 is immediately desorbed from the metal hydride 71 and piston 74 is pushed up or $H_2$ inflated. When metal hydride 71 is cooled, the hydrogen gas 70 is absorbed into metal hydride 71. Therefore, internal pressure decreases and piston 74 moves down. The piston can also be spring-loaded to quicken the action (not shown).

This metal hydride artificial muscle is driven by heat input, so the efficiency of the metal hydride actuator is important. The overall efficiency of the metal hydride actuator, $\eta_{MH}$, can be defined as, $$\eta_{MH} = \frac{P_{out}}{P_{in}}, \quad (4)$$

where $P_{out}$ and $P_{in}$ are power output generated and consumed electric power input, respectively. The power output generated, $P_{out}$, will be, $$P_{out} = \frac{W_{out}}{t_{op}}, \quad (5)$$

where $W_{out}$ is the output work generated during the period of actuation, $t_{op}$. The output work generated, $W_{out}$, is, $$W_{out} = \eta_0 Q_{in} - \Delta U_{MH+H_2} \quad (6)$$

where $\eta_o$, $Q_{in}$, and $\Delta U_{MH+H_2}$ are the overall efficiency associated with the thermo-electric device including heat transfer effects, or other types of heat input devices, the heat input, and the change of internal energy for both metal hydride and hydrogen, respectively. From Equations (4), (5), and (6), the efficiency of metal hydride actuators can be written as, $$\eta_{MH} = \frac{\eta_0 Q_{in} - \Delta U_{MH+H_2}}{t_{op} P_{in}}. \quad (7)$$

The estimated typical efficiency of the metal hydride actuator, $\eta_{MH}$, is approximately 60% when the actuation temperature is set at 30° C. with $LaNi_5$ selected as the metal hydride. If an appropriate hydride can be selected, the actuation temperature can be lowered, for example, Calcium-based metal hydride actuates at approximately −50° C. Note that one goal is to find $\eta_{MH}$ by building a device and measuring $\eta_{MH}$. The equilibrium pressure will be approximately 200–300 kPa (~2–3 atm). Then, the expected overall hydrogen volume generated, $\Delta v_g$, will be approximately 37–55 $cm^3$/g $LaNi_5$. Although the metal hydride actuator efficiency itself appears less than that of an electric actuator that uses electric power directly, and accounting for the necessary auxiliary components for the electric actuator, the power output per weight of the proposed metal hydride actuator is significantly large. Furthermore, the metal hydride artificial muscles can operate by waste heat. Hence, the metal hydride actuator is suitable for use as a space actuator with necessary features of having high specific-power and being lubricationless, noiseless, fast and smooth.

The present invention can also be used for deployable structures. FIG. 8A, 8B, 8C, and 8D show deployable structures using metal hydride artificial muscles. When heat is applied to the metal hydride 80, hydrogen gas 81 is immediately desorbed from the metal hydride 80 and hydrogen inflates deployable structure 82. When metal hydride 80 is cooled, hydrogen gas 81 is absorbed quickly by the metal hydride actuator body 83 with controller 84.

Figures 8A, 8B:
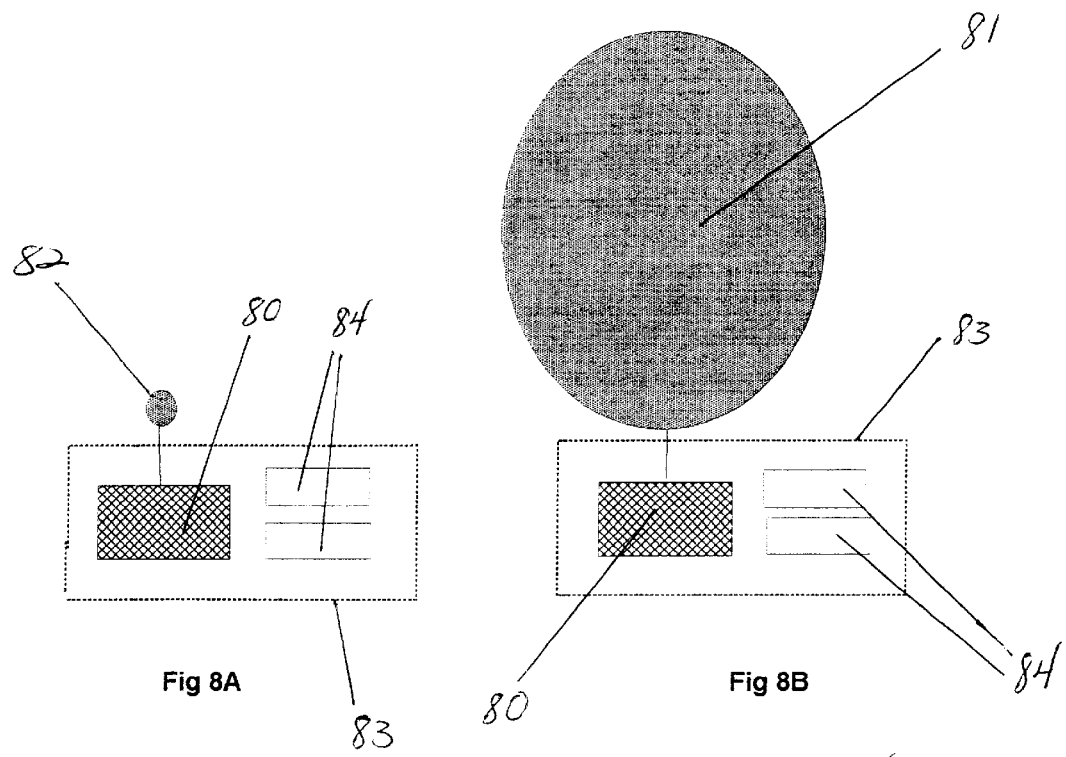
FIGS. 8A, 8B, 8C, and 8D show deployable structures using metal hydride artificial muscles.
Figures 8C, 8D:
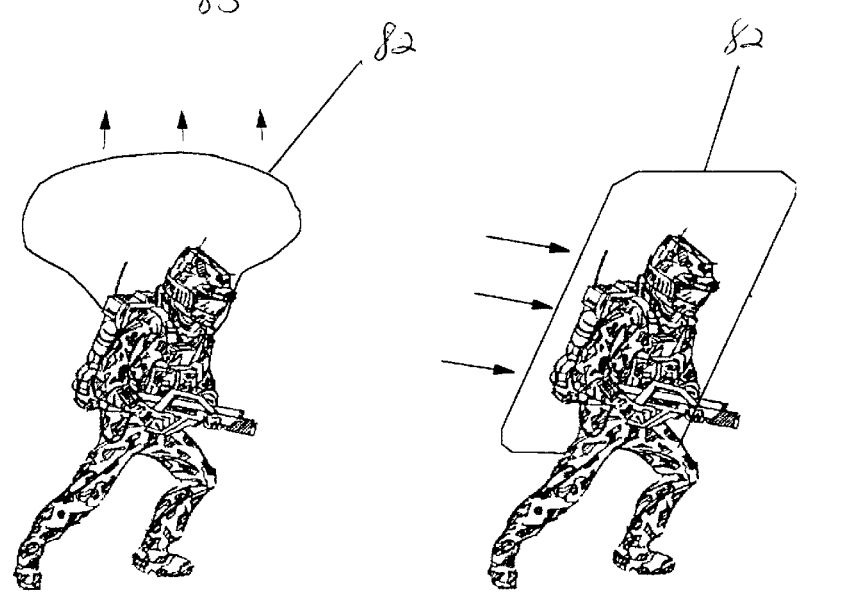

Effective soldier metal hydride systems meet the criteria of battlefield capabilities of "lethality, command/control, survivability, sustainment, and mobility." The metal hydride system provides large weight reduction capabilities to perform enhanced mission capabilities upon being burdened with advanced equipment. Also, it can function as a weight reduction system and actuator using hydrogen gas pressure from the metal hydride by any heat input, such as cigarette lighters, Joule-heating by electric input, and heat radiation panels. Specially designed deployable structures that contain the hydrogen gas can construct the functioning part. When heat is applied to the metal hydride, hydrogen gas is immediately desorbed from the metal hydride and hydrogen is inflated. When metal hydride is cooled by the ambient surroundings, the hydrogen gas is absorbed quickly by the metal hydride actuator body. For a soldier system application, as shown in FIGS. 8C and 8D, when hydrogen is acting, the deployed structure can provide a net lift force that is governed by the buoyancy. In this case, the deployed structure can function as an enhanced surface to improve the mobility of the soldier system.

Figure 9:
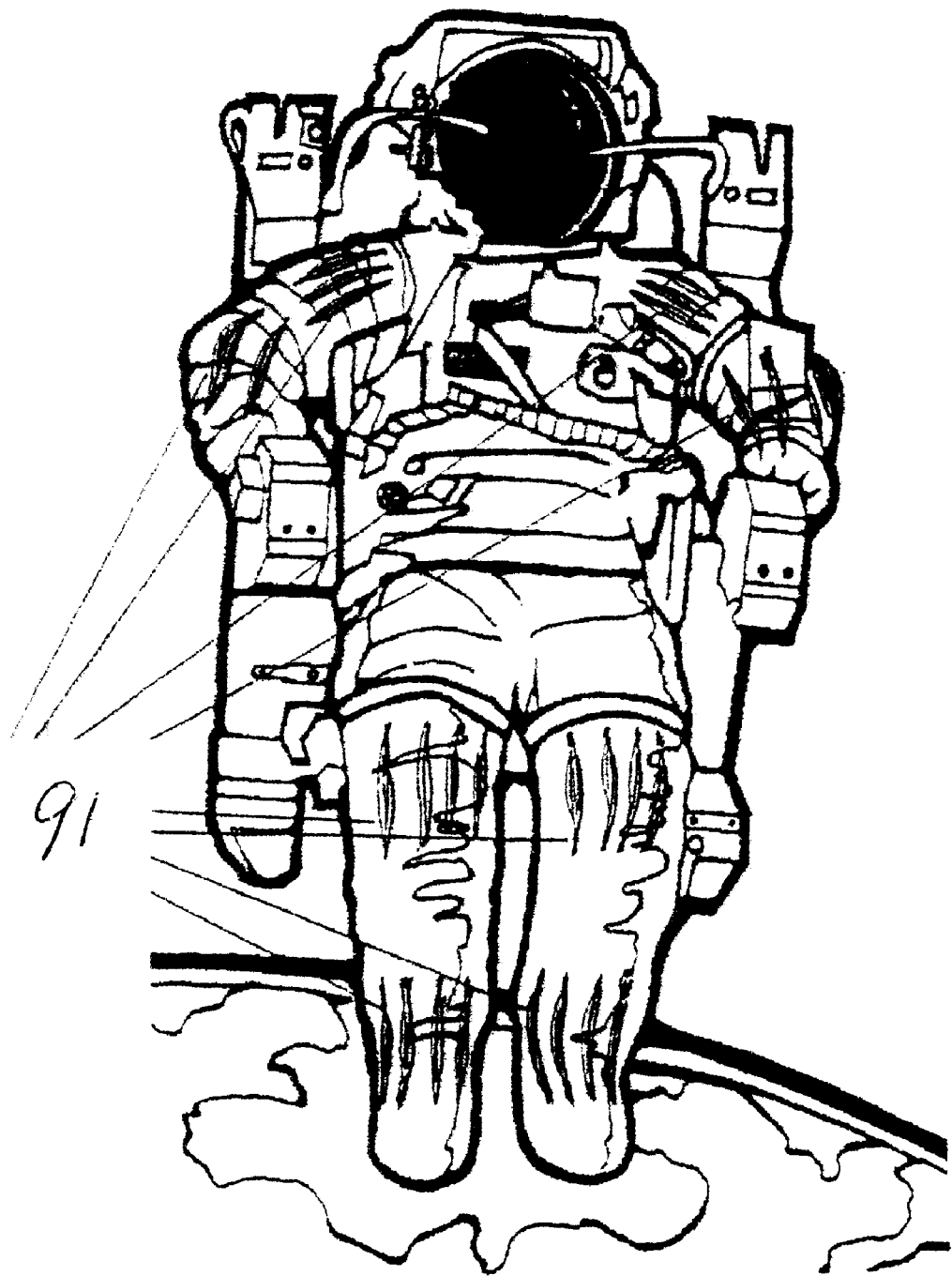
FIG. 9 is a joint power augmentation of astronauts using metal hydride artificial muscles.

A joint power augmentation of astronauts using metal hydride artificial muscles is shown in FIG. 9. As can be seen, thermally driven metal hydride systems 91 can augment an astronauts' regular and extra vehicular activities. The space cold environment is favorable for metal hydrides, therefore, the cooling is natural, resulting in an increased cycling time. The heating can be done by any means, as discussed above.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, are hereby incorporated by reference.

What is claimed is:

1. A metal hydride artificial muscle comprising:
   an expandable bladder;
   at least one metal hydride specimen encased within said expandable bladder; and
   a means to heat said at least one metal hydride.

2. The invention of claim 1 wherein said expandable bladder comprises a collapsible bladder.

3. The invention of claim 1 wherein said bladder comprises a hermetically sealed bladder.

4. The invention of claim 1 wherein said expandable bladder further comprises at least one actuator arm affixed to at least one part of said expandable bladder.

5. The invention of claim 4 further comprising spring loading said at least one actuator arm.

6. The invention of claim 1 wherein said at least one metal hydride specimen comprises encapsulated particles within said at least one metal hydride specimen.

7. The invention of claim 6 wherein said encapsulated particles comprise an encapsulated material comprising a thermally conductive medium.

8. The invention of claim 1 wherein said means to heat said at least one metal hydride comprises a controller.

9. The invention of claim 8 wherein said controller comprises a temperature sensor feedback loop.

10. The invention of claim 8 wherein said controller comprises a microprocessor.

11. The invention of claim 1 wherein said means to heat said at least one metal hydride specimen comprises an electric Joule heater.

12. The invention of claim 1 wherein said means to heat said at least one metal hydride specimen comprises a heater to heat said at least one metal hydride specimen above at least one critical temperature.

13. The invention of claim 1 wherein said means to heat said at least one metal hydride specimen further comprises a means to cool said at least one metal hydride specimen.

14. The invention of claim 13 wherein said means to cool said at least one metal hydride specimen comprises an apparatus to cool said at least one metal hydride specimen to below at least one critical temperature.

15. A method for actuating an object with a metal hydride artificial muscle, the method comprising the steps of:
   a) providing at least one metal hydride specimen in an expandable bladder;
   b) affixing at least one part of the expandable bladder to an actuator arm; and
   c) heating the at least one metal hydride specimen.

16. The method of claim 15 wherein the step of heating comprises heating the at least one metal hydride specimen above at least one critical temperature.

17. The method of claims 15 further comprising the step of cooling the at least one metal hydride specimen.

18. The method of claim 17 wherein the step of cooling comprises cooling the at least one metal hydride specimen below at least one critical temperature.

19. The method of claim 15 wherein the step of heating comprises controlling a heater.

20. The method of claim 19 wherein the step of controlling comprises sensing a temperature of the at least one metal hydride and feeding the sensed temperature to the controller.

21. The method of claim 15 further comprising the step of spring loading the at least one actuating arm.

22. The method of claim 15 wherein the step of providing at least one metal hydride specimen comprises encapsulating particles within the at least one metal hydride specimen with a thermally conductive medium.

23. A metal hydride artificial muscle for a biomedical and robotic applications comprising:
   an expandable bladder with a first end affixed to a first portion of a body and a second end affixed to a second portion of a body;
   at least one metal hydride specimen encased by said expandable bladder; and
   a means for heating and cooling said at least one metal hydride specimen.

24. A metal hydride artificial muscle for hydrogen gas aided take off, flying and landing of an object comprising:
   a bladder;
   at least one metal hydride specimen encased by said bladder; and
   a means for heating and cooling said at least one metal hydride specimen.

25. A metal hydride artificial muscle joint power augmentation system for external assistance of a person comprising:
   an expandable and collapsible bladder with a first end affixed to a first portion of the area to be augmented and a second end affixed to a second portion of the area to be augmented;
   at least one metal hydride specimen encased by said expandable and collapsible bladder; and
   a means for heating and cooling said at least one metal hydride specimen.

26. The invention of claim 25 wherein said joint power augmentation system comprises a joint power augmentation system for astronaut space suits.

* * * * *